(12) United States Patent  
Ansovini

(10) Patent No.: US 7,045,323 B2  
(45) Date of Patent: May 16, 2006

(54) GLUTATHIONE REDUCTASE FOR THERAPY AND PROPHYLAXIS OF AIDS

(76) Inventor: Raffaele Ansovini, Via dei Marcisi, 61/Q, 06100 Perugia (IT)

(*) Notice: Subject to any disclaimer, the term of this patent is extended or adjusted under 35 U.S.C. 154(b) by 135 days.

(21) Appl. No.: 10/863,367

(22) Filed: Jun. 9, 2004

(65) Prior Publication Data

US 2004/0223958 A1   Nov. 11, 2004

Related U.S. Application Data

(63) Continuation of application No. 09/979,194, filed as application No. PCT/EP00/02703 on Mar. 28, 2000, now abandoned.

(30) Foreign Application Priority Data

May 21, 1999   (IT) ............................. MI99A1122

(51) Int. Cl.  
*C12N 9/00*   (2006.01)
(52) U.S. Cl. ..................................... 435/183
(58) Field of Classification Search ................. 435/183  
See application file for complete search history.

(56) References Cited

U.S. PATENT DOCUMENTS

| 4,283,381 A | 8/1981 | Speck et al. |
| 5,827,886 A | 10/1998 | Hersh |
| 5,849,290 A | 12/1998 | Brown et al. |
| 6,313,164 B1 | 11/2001 | Fujita et al. |
| 6,368,629 B1 | 4/2002 | Watanabe et al. |

FOREIGN PATENT DOCUMENTS

WO   WO 00/71146 A3   11/2000

OTHER PUBLICATIONS

Simon, Gaëlle, et al., "Valpoic acid reduces the intracellular level of glutathione and stimulates human immunodeficiency virus," *Chemico-Biological Interactions* 91:111-121, 1994.

Palamara, Anna T., et al., "Inhibition of Murine AIDS of Reduced Glutathione," *AIDS Research and Human Retroviruses* 12(14):1373-1381, 1996.

O'Donovan, Donough J., et al., "Gene Transfer of Mitochondrially Targeted Glutathione Reductase Protects H441 Cells from t-Butyl Hydroperoxide-Induced Oxidant Stresses," *Am. J. Respir. Cell. Mol. Biol.* 20:256-263, 1999.

Ansovini, R., et al., "In Vitro Inhibition of Human Immunodeficiency Virus Type 1 (HIV-1) by FOY and Glutathione Reductase," AIDS Vaccine 2001 Conference, Philadelphia, PA., Sep. 5-8, 2001; Abstract/Poster 211. http://www.aidsvaccine2001.org/Pages/Abstract/10290.htm.

*Primary Examiner*—Michael Meller  
(74) *Attorney, Agent, or Firm*—Rothwell, Figg, Ernest & Manbeck, PC

(57) ABSTRACT

The present invention concerns the use of glutathione-reductase (GSSG reductase) for the preparation of a medicament for the treatment of HIV-infected patients, seropositive or already affected by AIDS, both for prophylactic and therapeutic use.

8 Claims, No Drawings

GLUTATHIONE REDUCTASE FOR THERAPY AND PROPHYLAXIS OF AIDS

This application is a continuation of application Ser. No. 09/979,194, filed Jan. 8, 2002, now abandoned which is a §371 of PCT/EP00/02703, filed Mar. 28, 2000, which claims the benefit of Italian Application No. MI 99 A001122, filed May 21, 1999.

FIELD OF THE INVENTION

The present invention concerns the use of glutathione-reductase (GSSG reductase) for the preparation of a medicament for the treatment of HIV-infected patients, seropositive or already affected by AIDS, both for prophylatic and therapeutic use.

BACKGROUND OF THE INVENTION

AIDS (Acquired Immune Deficiency Syndrome) may be considered a secondary immunodeficient pathology induced by Human Immunodeficiency Viruses or HIVs.

The immunological profile typical of AIDS, from the initial infection to the terminal stages of the disease, shows the effects of the gradual impairment of the immune system. In AIDS, the onset of cellular immunity and immune surveillance with consequent destruction of CD4+ T-cells allows the invasion of opportunistic organisms resulting in viral, bacterial, protozoal or fungal infections as well as the onset of virally induced tumors due to the lack of the immune cells which should suppress their appearance.

AIDS therapy is presently based on the use of anti-retroviral agents belonging to three categories.
HIV protease inhibitors;
Nucleoside reverse transcriptase inhibitors (NRTI);
Non-nucleoside reverse-transcriptase inhibitors (NNRTI).

Said drugs may be used alone or more frequently in combination.

The therapeutic approach based on vaccination is presently still at an experimental level, with interlocutory results. The therapy of patients affected by AIDS involves moreover the administration of agents suitable for treating said opportunistic infections.

A known aspect of HIV infection is the increase of oxidative stress which may contribute to enhance the replication of HIV itself, explaining at least partially the immunological anomalies connected to HIV pathology.

It was observed that the increase of oxidative stress in HIV infected patients is associated with the depletion of natural antioxidant agents, particularly of reduced glutathione (GSH).

It has also been experimentally shown that GSH and N-acetylcysteine can inhibit the HIV reverse transcription process (M. Kameoka et al., *AIDS Res. Hum. Retroviruses* 12: 1635-8 (1996)) and that GSH administered in a murine model of immunodeficiency is able to decrease the proviral DNA load in the first stage of infection (A. T. Palamara et al., *AIDS Res. Hum. Retroviruses* 12: 1373-81 (1996)). Notwithstanding these results, the use of GSH has never been proposed for therapeutic treatment of AIDS.

It has now been surprisingly found that the administration of glutathione reductase can restore the natural immune defenses and can validly contribute in preventing HIV-induced pathology and in treating it in already infected patients.

SUMMARY OF THE INVENTION

The present invention refers to the use of glutathione reductase (GSSG reductase) for the preparation of a medicament for the treatment and prevention of HIV infections.

The invention also concerns pharmaceutical compositions containing an effective amount of glutathione reductase in admixture with suitable carriers.

According to a third embodiment, the invention concerns pharmaceutical compositions containing glutathione reductase and at least one medicament selected from the classes of HIV proteases inhibitors, nucleoside reverse transcriptase inhibitors (NRTI) or non-nucleoside reverse-transcriptase inhibitors (NNRTI) for simultaneous, separate or sequential administration.

DETAILED DESCRIPTION OF THE INVENTION

It has been found that glutathione reductase is surprisingly able to inhibit the HIV viral cycle.

The ability of an electron-carrying enzyme to interfere with the viral cycle has never been disclosed and provides an entirely new therapeutic approach to the problem of AIDS treatment and prevention.

The activity of GSSG reductase has been shown, inter alia, using well established in vitro models of chronic infections of human cell lines (both T-cells and monocytes-macrophages) in which viral expression can be induced by several cytokines (TNF-alpha, IL-6, IL-1 beta, IFN-gamma) or by phorbol esters. Glutathione reductase, added to the medium in a range of 6 scalar concentrations (log10), interferes with the HIV replication control while exerting no toxicity on either primary cells or on chronically infected cell lines.

The same results were obtained using experimental models of acute infections in PHA blasts or monocyte-derived macrophages infected by IIIB (CXCCR4-dependent) and BaL (CCR5-dependent) HIV strains.

It can be hypothesised that GSSG reductase is able to counteract the cytotoxic allosterism occurring in some HIV proteins, particularly in the NCp7 protein, following impairments of cellular metabolic pathways dependent on the NAD/NADPH ratio. The validity of the invention is not anyhow bound to the actual verification of this hypothesis.

Glutathione reductase is a ubiquitous enzyme catalyzing the reduction of oxidized glutathione (GSSG) to glutathione (GSH).

Glutathione reductase is a homodimeric enzyme belonging to the family of flavoprotein disulfide oxidoreductases which can be extracted from several sources (human erythrocytes, mammalian liver, bacteria or yeasts) and has a molecular weight ranging from 100,000 and 118,000 daltons.

Glutathione reductase is commercially available, e.g. from Sigma-Aldrich Fine Chemicals, or it may be obtained by known methods, either by extraction or by recombinant DNA methods.

In substitution of the enzyme, compounds having agonist activity or which are able to stimulate the production of glutathione reductase, acting for example on the transcription control elements of the corresponding gene, may also be used.

For the considered therapeutic use, the enzyme may be formulated into suitable pharmaceutical compositions using known methods and carriers, as disclosed for instance in Remington's Pharmaceutical Sciences Handbook, Mack Pub. Co., NY, USA, XVII Ed.

The compositions of the invention preferably are administered by the intravenous or inhalatory route. Examples of suitable formulations include ready-to-use vials containing sterile solutions, vials containing the lyophilized enzyme combined with a separate vial containing a suitable sterile solvent for the lyophilized enzyme and other conventional parenteral formulations.

The oral administration can also be envisaged, using for instance liposomal formulations or other known methods allowing the oral administration of protein substances.

In addition to GSSG reductase, the parenteral compositions may also comprise suitable excipients such as sodium edetate, sodium glutamate, polygelin together with a suitable organic (e.g. tromethamol) or inorganic (e.g. mixed phosphates) buffer, so as to secure a pH value ranging from 6.5 to 7.6.

The lyophilization of the enzyme can be carried out by known methods using suitable carriers such as lactose, mannitol, phosphates and the like whereas the solvent, in addition to saline solution, may contain suitable preserving agents, such as alkyl p-hydroxybenzoates and the above cited buffer solutions.

The daily posology will be usually comprised between 1 and 10 mg of enzyme, preferably 1.5–2.5 mg once or more times a week, preferably twice a week, until normalization of the plasma concentration of GSH is obtained.

GSSG reductase also can be used advantageously in combination with the presently available anti-HIV treatments, particularly in combination with HIV proteases inhibitors, nucleoside reverse transcriptase inhibitors (NRTI) or non-nucleoside reverse-transcriptase inhibitors (NNRTI).

Integrase inhibitors as well as protease inhibitors such as camostat (FOY-305) or similar compounds (aprotinin, gabexate, sepimostat) also can be effectively administered in combination with GSSG. The posology of the GSSG reductase is the same as detailed before whereas that of the other agents can be the same as used in conventional protocols or it may also be reduced, in view of the synergistic effect induced by the administration of GSSG reductase.

Examples of HIV protease inhibitors include saquinavir, indinavir, ritonavir, nelfinavir, BMS-232632.

Examples of reverse transcriptase inhibitors include azidothymidine (AZT), dideoxycytidine, dideoxyinosine (DDI), and stavudine.

The combined treatment of camostat or a salt or metabolite thereof and GSSG reductase is particularly preferred.

The invention provides therefore pharmaceutical compositions in the form of combined preparations for simultaneous, separate or sequential use in AIDS therapy or prevention, comprising glutathione reductase and at least one anti-HIV agent selected from HIV proteases inhibitors, nucleoside reverse transcriptase inhibitors (NRTI), non-nucleoside reverse-transcriptase inhibitors (NNRTI), integrase inhibitors, camostat or other proteinase inhibitors.

Examples of compositions of the invention are herein below reported.

EXAMPLE 1

Ready-to-use vials for intravenous injections comprising:

| | |
|---|---|
| glutathione reductase from yeasts: | 2 mg |
| sterile saline solution | 3 ml |

EXAMPLE 2

Vials for intravenous administration to be dissolved immediately prior to administration comprising:

| | |
|---|---|
| lyophilized glutathione reductase from human erythrocytes: | 2.5 mg |
| vial containing sterile saline solution: | .5 ml |

EXAMPLE 3

Composition in the form of kit-of-parts comprising:
a vial of Example 1 or 2;
tablets of camostat mesylate (600 mg per unit dose).

The invention claimed is:

1. A method of treating a patient infected with HIV which comprises administering to said patient a therapeutically effective amount of both glutathione reductase and camostat or a pharmaceutically acceptable salt or metabolite thereof, wherein said glutathione reductase is administered intravenously in an amount of 1 mg to 10 mg and said camostat is administered orally.

2. A method of claim 1 wherein said glutathione reductase and said camostat are administered simultaneously.

3. A method of claim 1 wherein said glutathione reductase and said camostat are administered sequentially.

4. A method of claim 1 wherein said glutathione reductase is formulated with a pharmaceutically acceptable buffer having a pH of 6.5 to 7.6 and an excipient selected from the group consisting of sodium edetate, sodium glutamate, polygelin and a combination thereof.

5. A method of claim 4 wherein said glutathione reductase formulation further comprises a pharmaceutically acceptable preserving agent.

6. A method of claim 1 wherein said glutathione reductase is lyophilized.

7. A method of claim 1 wherein said camostat or a pharmaceutically acceptable salt or metabolite thereof is camostat mesylate.

8. A method of claim 1 wherein said camostat or a pharmaceutically acceptable salt or metabolite thereof is formulated as a tablet.

* * * * *